United States Patent [19]

Lopatinsky

[11] Patent Number: 5,600,752
[45] Date of Patent: Feb. 4, 1997

[54] FLEXIBLE GAS HOSE ASSEMBLY WITH CONCENTRIC HELICAL TUBE MEMBERS HAVING REINFORCEMENT SPRING COILS

[75] Inventor: Edward Lopatinsky, Los Angeles, Calif.

[73] Assignee: Industrial Design Laboratories, Inc., Chula Vista, Calif.

[21] Appl. No.: 212,166

[22] Filed: Mar. 11, 1994

[51] Int. Cl.$^6$ ............ A61M 16/00; H05B 3/00; F24H 1/10
[52] U.S. Cl. ............ 392/488; 392/472; 138/33; 138/122; 138/134; 138/114; 138/173; 174/47
[58] Field of Search ............ 392/488, 489, 392/486, 472, 478, 480; 219/535, 531; 138/33, 121–122, 133, 134, 114, 173; 128/204, 17; 374/148; 73/204.11, 204.12; 174/47

[56] References Cited

U.S. PATENT DOCUMENTS

| | | | |
|---|---|---|---|
| 1,535,376 | 4/1925 | Race | 392/472 |
| 1,995,302 | 3/1935 | Goldstein | 392/470 |
| 2,809,268 | 10/1957 | Heron | 392/480 |
| 3,037,798 | 6/1962 | Cooper | 138/121 |
| 3,076,737 | 2/1963 | Roberts | 156/144 |
| 3,275,803 | 9/1966 | True | 219/535 |
| 3,293,407 | 12/1966 | Ando | 392/480 |
| 3,378,673 | 4/1968 | Hopper | 392/472 |
| 3,383,875 | 5/1968 | Haas | 138/113 |
| 3,638,926 | 2/1972 | Melville et al. | 261/130 |
| 3,706,208 | 12/1972 | Kadi et al. | 138/114 |
| 4,038,519 | 7/1977 | Foucras | 219/505 |
| 4,098,298 | 7/1978 | Vohrer | 138/122 |
| 4,121,623 | 10/1978 | Rhone | 138/114 |
| 4,130,904 | 12/1978 | Whalen | 138/122 |
| 4,445,543 | 5/1984 | Mead | 138/122 |
| 4,570,678 | 2/1986 | Ziemek et al. | 138/113 |
| 4,650,471 | 3/1987 | Tamari | 138/114 |
| 4,686,354 | 8/1987 | Makin | 219/535 |
| 4,967,744 | 11/1990 | Chua | 128/204.17 |

FOREIGN PATENT DOCUMENTS

| | | | |
|---|---|---|---|
| 161709 | 3/1955 | Australia | 392/488 |
| 193030 | 11/1957 | Austria | 392/488 |
| 1429597 | 1/1966 | France | 392/472 |
| 677891 | 6/1939 | Germany | 138/122 |
| 2161839 | 6/1973 | Germany | 138/121 |
| 3149623 | 7/1983 | Germany | 392/488 |
| 262803 | 12/1927 | United Kingdom | 392/488 |
| 527759 | 10/1940 | United Kingdom | 392/480 |
| 799547 | 8/1958 | United Kingdom | 392/472 |

*Primary Examiner*—John A. Jeffery
*Attorney, Agent, or Firm*—Edward Dreyfus

[57] ABSTRACT

A flexible hose assembly for conveying gas comprising an inner tube member having a reinforcing spring coil that selectively functions as an electric heater engaging the inner surface and an outer flexible tube member having its head and outlet ends closed upon those of the inner member. A second reinforcing spring coil surrounds the outer surface of the outer member such that a dead air space or insulating chamber is formed between the two flexible tubes. Superior insulation, flexibility, energy consumption, weight and strength characteristics are achieved. A temperature responsive electrical device can be mounted near the outlet end of the inside wall of the inner tube with leads extending through the hose exiting the head end for connection to a controller for controlling an external heating or cooling system or for controlling electric power applied to the inner spring coil for directly heating the flowing gas for delivering temperature controlled heated gas to the end user system. The air in the chamber can be less than one atmosphere to enhance the insulating function.

21 Claims, 5 Drawing Sheets

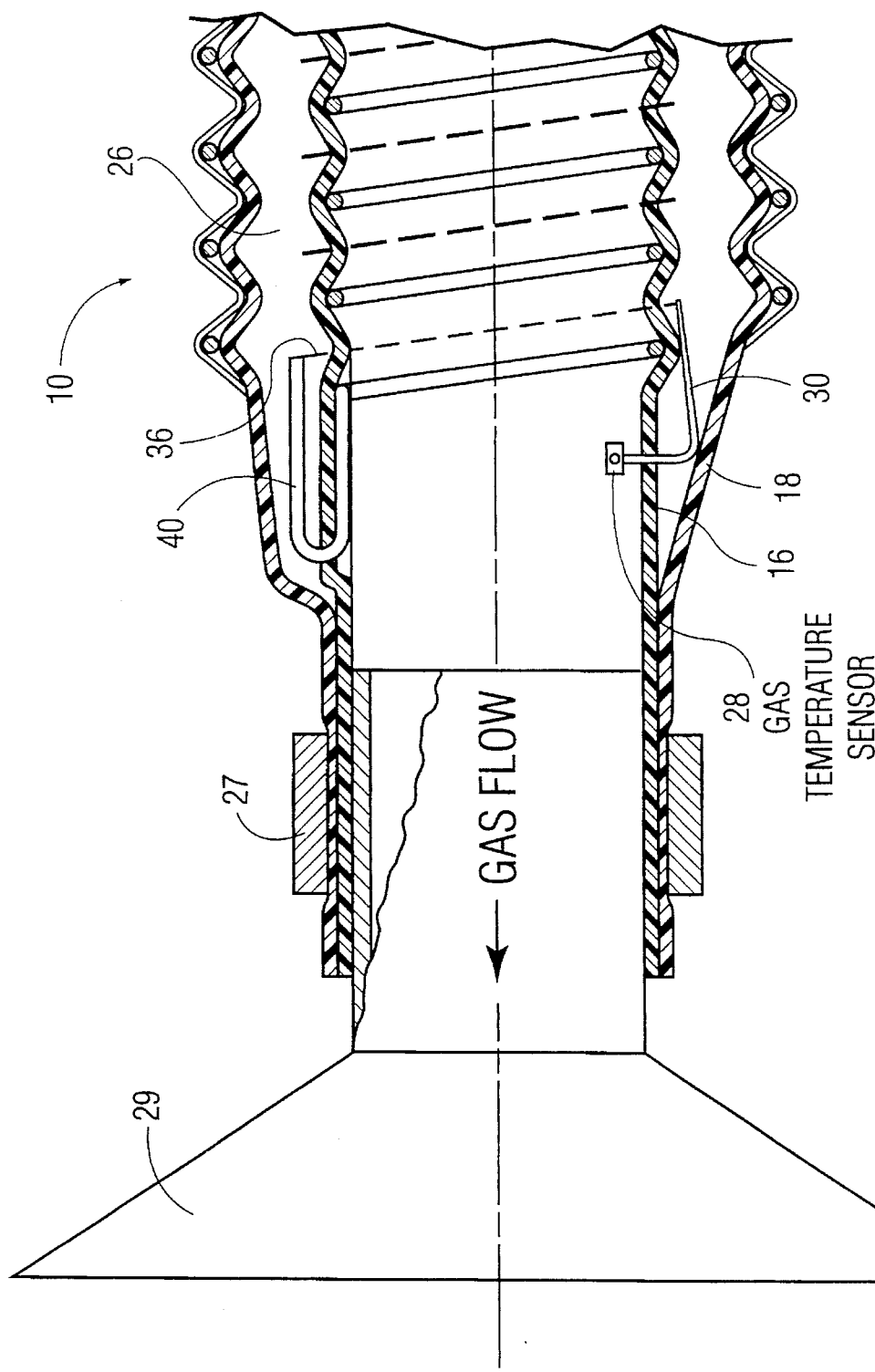

FLEXIBLE GAS HOSE ASSEMBLY WITH CONCENTRIC HELICAL TUBE MEMBERS HAVING REINFORCEMENT SPRING COILS

BACKGROUND

Flexible hoses are well known for conveying gas in a wide variety of applications, both military and civilian.

One standard approach includes providing a flexible tube with insulating material surrounding the same to provide strength and to reduce heat transfer between the flowing gas and the ambient. A disadvantage with this standard design is that often the insulation detracts from the flexibility of the system, adds to weight, and may not contribute significantly to longitudinal tensile and compression strengths of the system.

An attempted standard improvement comprises adding a spring coil to increase strength parameters and perhaps reduce the thickness requirement of the insulation layer depending upon the particular application of the hose assembly.

Where the application requires temperature control, standard hoses are normally coupled to a system that includes a thermocouple device and a controller for sensing the gas temperature before it enters the head end of the hose and applying electric power to the heating elements located before such head end. These systems are somewhat unreliable particularly where the delivery hose branches to a number of users of the gas supply or where the length of hose enables significant exchange between ambient and the flowing gas or where the ambient temperature can vary over a significant range.

One such application where these problems arise is in air supply hoses to crew members of tanks and other military vehicles.

These and other problems are avoided with the hose assembly according to the present invention.

SUMMARY OF EXEMPLARY EMBODIMENT OF THE INVENTION

An exemplary embodiment according to one aspect of the present invention includes an inner flexible tube member and an outer flexible tube member spaced from each other to form an insulating air chamber about the inner tube member. A spring coil lines one of the surfaces of the inner member and another spring coil lines one of the surfaces of the outer tube member. Tape or other suitable material can be applied to cover the outer tube member and the outer spring coil.

According to another aspect of the present invention, the hose can include a thermocouple or thermistor device or other temperature sensing device located near the hose outlet or delivery end so that gas temperature near the user can be monitored. Leads for the device extend from the device through the hose length to the controller. All or a portion of the leads can be wrapped around the inner member for enhancing the flexibility of the tube assembly.

According to another aspect of the invention, the tube members in longitudinal section form undulation-like surfaces between or coincident with the longitudinally spaced spring coil segments for further enhancing the flexibility of the hose assembly.

According to another aspect of the invention, the electric power leads enter the hose at the head end. One power lead is coupled to the spring coil at the head end and the other power lead is coupled to the spring coil at the other end of the spring coil. Thus the inner spring coil not only provides strength, rigidity, and flexibility to the inner tube member, but can also function as the heating element for gas temperature control.

Some of the benefits of the embodiments include providing a hose with superior (i) strength and insulating characteristics, even for long or multiple hose lengths while using air, instead of some other more costly and dense material, as the insulator, (ii) temperature sensing device location for more accurate and reliable gas temperature control to the end user, and (iii) multi-functionality of parts and performance including reduction of energy consumption during operation for a given flow rate and temperature requirement and for various ambient conditions.

BRIEF DESCRIPTION OF THE DRAWINGS

Other and further benefits, objects, and advantages will become apparent with the following detailed description when taken in view of the appended drawings, in which:

FIGS. 4 and 5 are enlarged schematic views of parts of FIG. 3.

DETAILED DESCRIPTION OF AN EXEMPLARY EMBODIMENT OF THE PRESENT INVENTION

Figure 1:
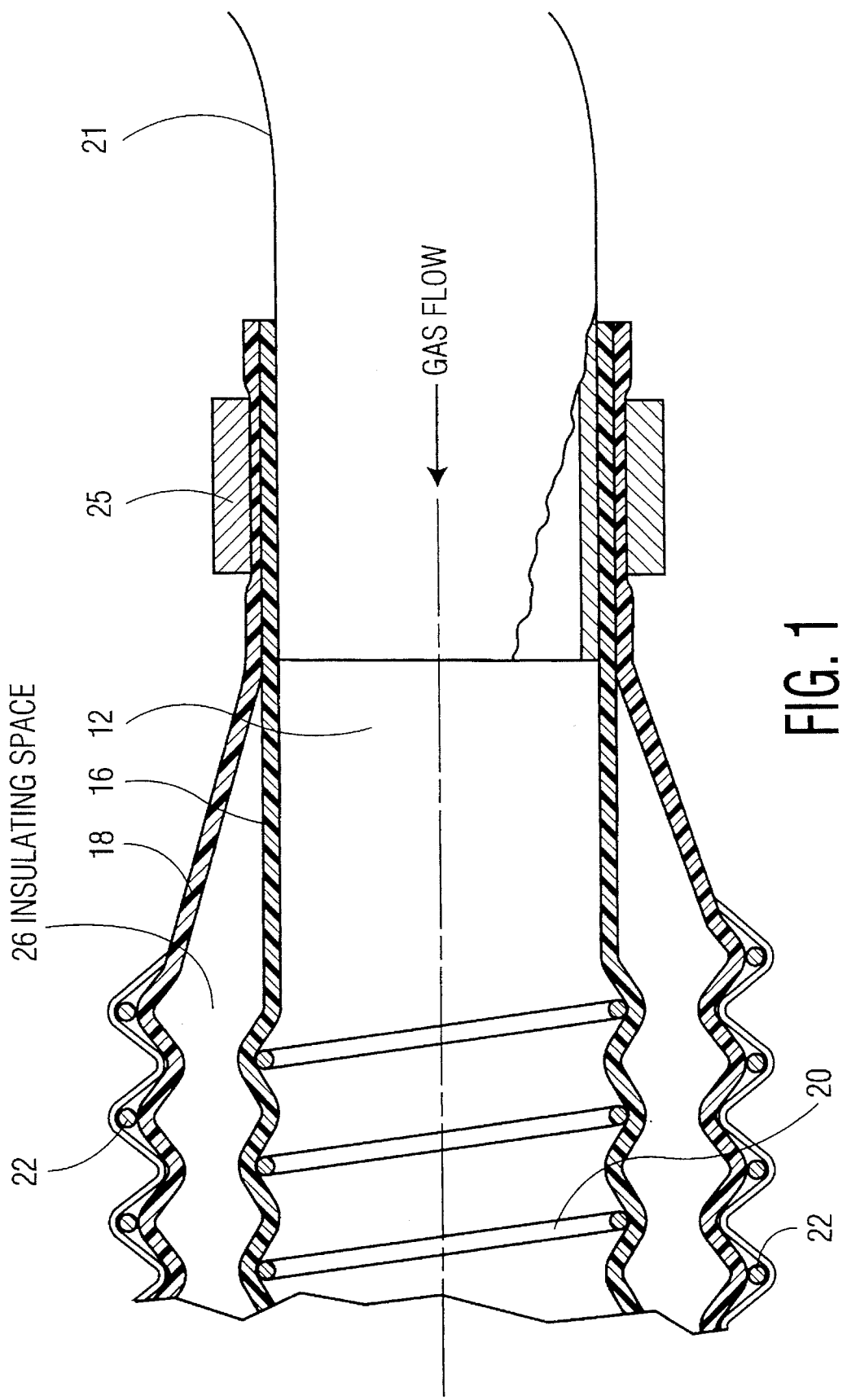
FIG. 1 is a schematic of a vertical, longitudinal section of the head end of a hose according to the present invention.
Figure 2:
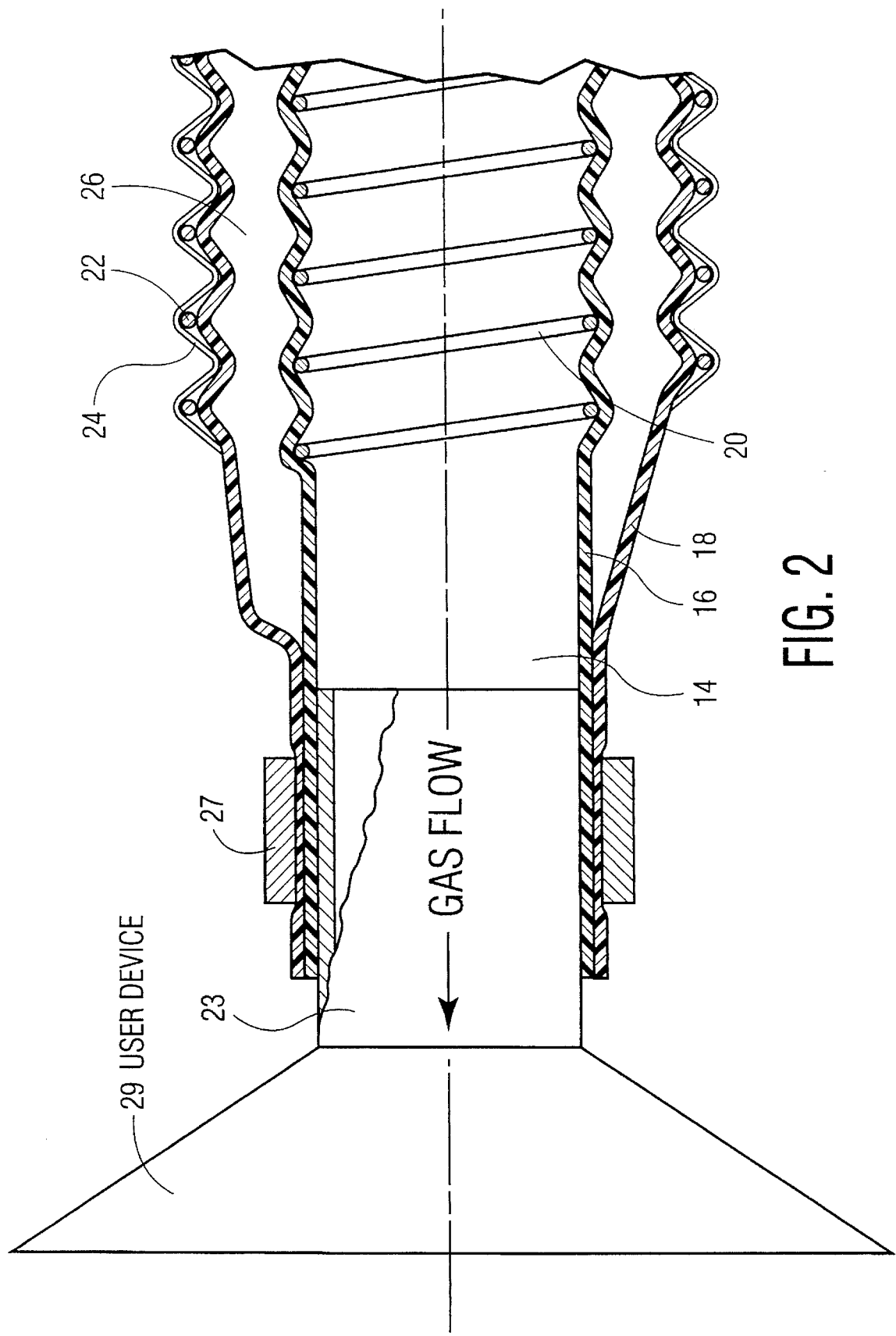
FIG. 2 is a similar schematic view of the outlet or delivery end of the hose of FIG. 1.

With reference to the FIGS. 1 and 2, a hose 10 includes an inner flexible tube 16 having a generally elongated, cylindrical form with a gas inlet or head end 12 and a gas outlet or delivery end 14. An inner spring coil 20 is arranged inside and along the inner walls of tube 16 to provide compression and elongation strength and to enable flexibility while holding the generally cylindrical shape of tube 16. Coil 20, if desired, could be arranged on the outside surface of tube 16.

A second flexible tube member 18 surrounds tube 16, and also includes head and outlet ends formed to close onto respective ends of tube 16 generally as shown. Another spring coil 22 engages one of the surfaces, such as outer surface as shown, of outer tube member 18 to provide similar functions mentioned above for spring coil 20. Tube 18 and coil 22 are dimensioned so that an enclosed, sealed air space or chamber 26 is formed between the outer surface of tube 16 and the inner surface of tube 18 and maintained by the supporting forces of coils 20 and 22. Preferably, the air in chamber 26 is under vacuum or below one atmosphere which enhances the insulating function of the hose assembly.

The surfaces of tube members 16 and 18 form undulations between or coincident with the spaced segments of the spring coils, generally as shown. This arrangement enhances flexibility of the hose assembly to accommodate the concentric, double tube construction.

The outer surface of tube 18 and coil 22 can be covered for protection by a layer of tape and for aesthetic purposes by an outer layer of STOCINET covering the tape layer, both shown as 24 in the figures. STOCINET is a well known nylon fabric tube material normally made in accordance with Military Specification SPEC MIL-H-14506.

The various parts may be made of any well known materials. Spring coils 20 and 22 can be made of spring steel or other suitable metal. Tubes 16 and 18 may be made of rubber, plastic or other suitable flexible material. Tape 24 can comprise a commonly known brand called POLICAN. POLICAN is a common brand name for impregnated fabric tape and can be obtained as Tape No. 113 or 114 from the POLICAN Division of the Kendal Company, Boston, Mass. 02102.

In operation, the head and outlet ends of hose 10 are fitted over gas outlet and user receiving pipes 21 and 23, respectively, and secured to them in a conventional manner, such as by clamps 25 and 27. This clamping action further increases the sealing effect between tubes 16 and 18 forming chamber 26. Longitudinal, compression, and torque strengths are provided by the inner and outer spring coils and the cooperating double tube design. Thermal losses or exchanges between the gas flow and the ambient are reduced by the dead air chamber surrounding the inner tube member and the insulating value of the tube member materials.

Figure 3:
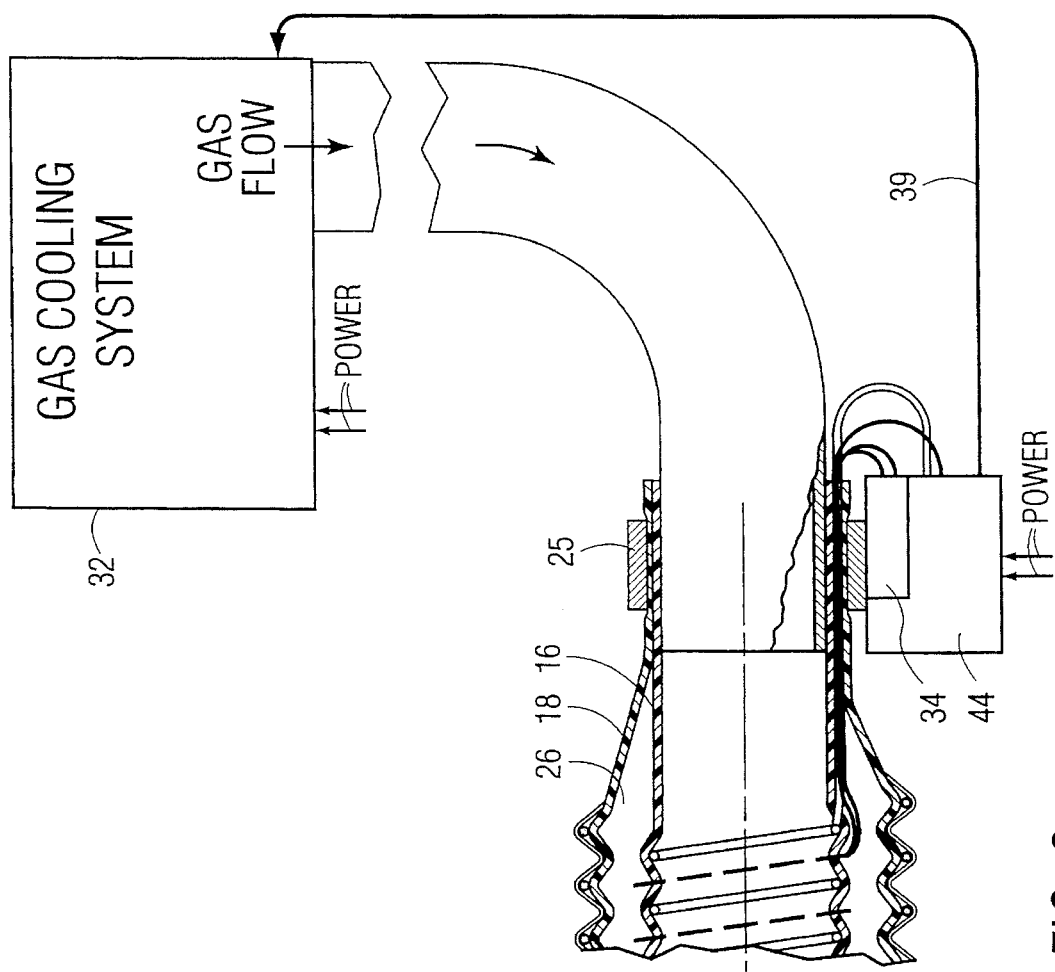
FIG. 3 is a schematic of a hose according to the invention and an external heating and/or cooling system coupled thereto.
Figure 4:
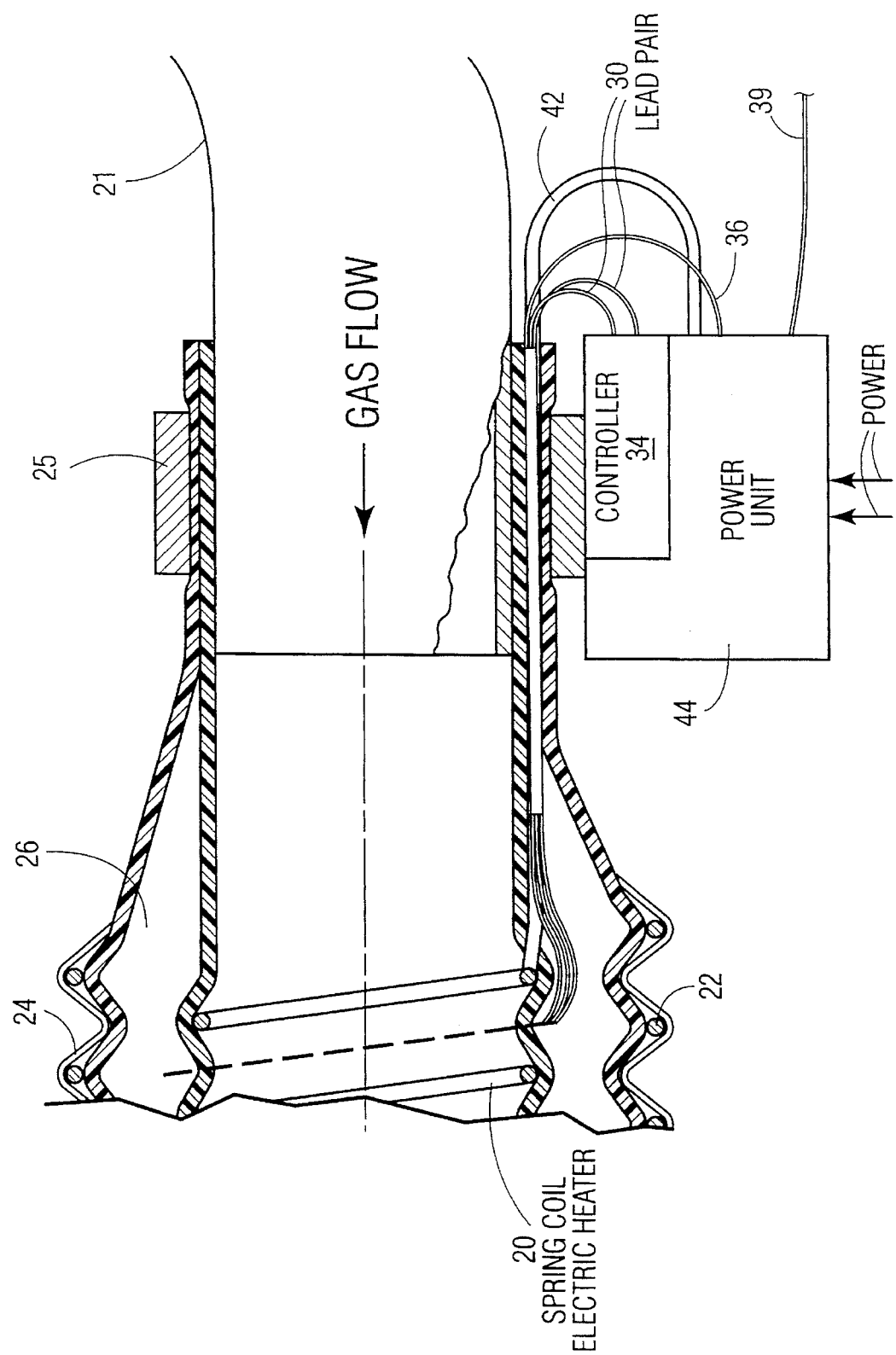

In an alternate embodiment, shown in FIGS. 3–5, capable of providing temperature control to the internal gas, a thermal device 28, such as a thermocouple, thermistor, or other suitable device is secured to the inside the wall of tube 16 preferably in direct contact with the gas internal to tube 16. Device 28 can be located in any desired longitudinal position depending upon the hose application, however, it is preferably located near the user device 29 or outlet end of tube 16 so that delivered gas temperature can be more reliably sensed. An electric lead pair 30 extends from device 28, through a small sealing opening in the tube 16 wall, along the length of chamber 26, between the sealed or contacting head ends of tubes 16 and 18 where it exits hose 10 and is electrically coupled to a controller 34 in the usual manner. Lead pair 30 and, as mentioned below, power lead 36 are preferably wrapped around inner tube member 16 along the spiral undulations generally as shown by the dashed lines. This arrangement assures that the length of the leads 30 and/or 36 will not inhibit the flexibility of the hose assembly 10.

When hose 10 is used with an external gas cooling system 32, controller 34 controls the powered operation of system 32 over lead 39 pursuant to well known techniques and responsive to delivered gas temperature indications on leads 30. Controller 34 can be any suitable standard and well known controller available in the industry.

Hose 10 of FIG. 3 can also be made capable of heating the gas under controlled conditions. Electrical power leads are soldered or otherwise connected to points spaced along spring coil 20. As seen in FIG. 4, the outlet end 40 of coil 20 extends through a small sealed opening of tube 16 and into chamber 26. Power wire 36 is soldered to coil end 40 and extends the length of chamber 26 exiting hose 10 between the head ends of tubes 16 and 18. Like or with leads 30, power wire 36 is wrapped around the tube member 16. The head end of coil 20 includes a longitudinal part 42 that also extends through a sealed opening of tube 16 and exits hose 10 between the head ends of tubes 16 and 18. Lead 36 can then be connected to an electrical power unit 44 and the free end of part 42 is connected thereto directly, as shown.

In operation, controller 34 determines delivery gas temperatures and applies control signals to unit 44 according to a predetermined algorithm. Electric power is then selectively applied to coil 20 that functions as a heating coil to warm the internal gas as desired.

It will be understood that any suitable method of manufacture or assembly may be used to implement the present invention. One example includes:

1. Slide spring 20 onto a mandrel and secure the ends thereto.
2. Slide natural rubber over the coil 20 and penetrate end 40.
3. Wrap twine or rope over the rubber which will cause the undulations to form in tube 16.
4. Place in an autoclave for 6–9 minutes at curing temperature.
5. Allow to cool, remove the rope.
6. Attach thermistor 28 with glue or adhesive, run leads 30 through small opening in tube 16, solder power wire to end 40, wind all leads around the length of tube 16.
7. Slide larger diameter natural rubber over a different mandrel,
8. Slide outer spring coil 22 over outer surface of outer tube 18 and secure the ends,
9. Overlay with protective POLICAN tape, overlay again with STOCINET.
10. Wrap rope over the STOCINET which will cause the undulations to form in tube 18,
11. Place in autoclave for 6–9 minutes at curing temperature, remove and allow to cool.
12. Slide outer tube subassembly over inner tube subassembly that is still on the mandrel, wrap rope again tightly over the outer tube subassembly to compress the rubber between the segments of spring coil 22, then glue engaging surfaces of the respective ends of tubes 16 and 18 and secure with clamps,
13. Place in autoclave for 40 minutes at curing temperature, remove, allow to cool, remove clamps, rope and mandrel, which enables the rubber between segments of spring coil 22 to expand.

In a preferred embodiment, air within chamber 26 expands during the curing or heating step 13 and escapes between the clamped surfaces of tubes 16 and 18 before they are entirely sealed. Thus, a sealed vacuum forms when the assembly cools and spring coil 22 and tube 18 material expand with the removal of the last mentioned rope, thereby expanding the volume of sealed chamber 26.

It will be understood that various modifications can be made to the embodiments herein disclosed without departing from the spirit and scope of the present invention and that the drawings are not necessarily drawn to scale.

I claim:

1. A flexible hose assembly for conveying gas comprising,
    a flexible tube member having an inlet end and an outlet end for receiving, conveying, and delivering a gas flow,
    a metal spring coil member arranged along a substantial length of said tube member and in substantial engagement with the inner surface thereof for providing axial and compression strength to said tube member,
    said coil member being in direct contact with the gas flow throughout a substantial length of said tube member,
    a temperature sensing device within said tube member and in direct contact with the gas flow for sensing the temperature of gas when flowing therein, and
    means coupled to said device for transmitting from said device to apparatus external to the hose assembly signals indicative of the gas flow temperature, and
    wherein said device is arranged near the outlet end of said tube member for sensing the gas temperature of the gas that is about to exit the hose assembly and said signals are indicative of the temperature of the gas that is about to exit the hose assembly, and wherein said means for transmitting signals indicative of the gas temperature comprises electrical leads extending from said device longitudinally through said tube member and axially in contact with a surface of said tube member and adjacent the inlet end of said tube member for connection to apparatus external to the assembly, and wherein said tube member comprises spiral undulations along its length and said leads are wrapped along said undulations.

2. An assembly according to claim 1, wherein said leads extend through the surface of said tube member and are wrapped about the outer surface of said tube member for a substantial portion of its length.

3. An assembly according to claim 1, further comprising electrical power means coupled to said coil member for applying electrical power to heat said coil member.

4. An assembly according to claim 3, wherein said electrical power means comprises first power wire means connected to one part of said coil member and second power wire means connected to another part of said coil member spaced from said one part.

5. An assembly according to claim 4, wherein said one part and said another part are located near the outlet and inlet ends of the coil member, respectively.

6. An assembly according to claim 5, wherein said one part extends through said tube member surface and said electrical power means is connected thereto external to said tube member and is wrapped around said tube member through the substantial length thereof.

7. An assembly according to claim 6, wherein said power wire is wrapped along with said leads.

8. An assembly according to claim 1, further including a second flexible tube member surrounding the first tube member and having its inlet and outlet ends closed on those of said inner tube member and having its inner surface spaced from the outer surface of the inner tube member to form an enclosed air space therebetween.

9. An assembly according to claim 8, wherein said assembly further comprises a second coil member that engages said outer tube member to provide axial and compression strength to said outer tube member.

10. An assembly according to claim 9, wherein said outer tube member comprises undulating surfaces.

11. An assembly according to claim 10, wherein said second coil member engages said outer tube member at the outer portions of the undulations thereof.

12. An assembly according to claim 11, wherein said inner tube member comprises spiral undulations and said first coil member engages said inner tube member at the outer portions of the undulations thereof.

13. An assembly according to claim 12, wherein said first coil member engages the inner surface of said undulations.

14. An assembly according to claim 8, wherein said air space is sealed to form an enclosed, sealed chamber.

15. An assembly according to claim 14, wherein the chamber comprises less than one atmosphere of gas pressure therein.

16. An assembly according to claim 8, wherein said leads extend between the facing surfaces of the inlet ends of the inner and outer tube members respectively.

17. A flexible hose assembly for conveying gas comprising, an inner flexible tube member having spiral undulating surfaces and inlet and outlet ends, an outer flexible tube member having spiral undulating surfaces surrounding said inner tube member and having inlet and outlet ends that close on the respective ends of said inner tube member, and the surfaces of said inner and outer members being spaced from each other along a major portion of their lengths to form an insulating air space about said inner tube member, reinforcement coil means for providing axial strength and compression strength to the flexible hose assembly, and wherein said reinforcement coil means comprises a first metal spring coil member extending continuously along a major portion of the length of the assembly and engaging said inner tube member and a second metal spring coil member that engages said outer tube member.

18. An assembly according to claim 17, wherein said outer coil member engages said outer tube member at the outer portions of the undulations thereof.

19. An assembly according to claim 17, wherein said first coil member engages said inner tube member at the outer portions of the undulations thereof.

20. An assembly according to claim 19, wherein said first coil member engages the inner surface of said undulations.

21. An assembly according to claim 17 wherein said air space is sealed to form an enclosed, sealed chamber, and wherein the chamber comprises less than one atmosphere of gas pressure therein.

* * * * *